US012491308B2

(12) United States Patent
Locke et al.

(10) Patent No.: US 12,491,308 B2
(45) Date of Patent: Dec. 9, 2025

(54) DRESSING INCLUDING OUTLET CONNECTION FLUID BUFFER

(71) Applicant: Solventum Intellectual Properties Company, Maplewood, MN (US)

(72) Inventors: Christopher Brian Locke, Bournemouth (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 103 days.

(21) Appl. No.: 17/602,608

(22) PCT Filed: May 6, 2020

(86) PCT No.: PCT/IB2020/054280
§ 371 (c)(1),
(2) Date: Oct. 8, 2021

(87) PCT Pub. No.: WO2020/229951
PCT Pub. Date: Nov. 19, 2020

(65) Prior Publication Data

US 2022/0184294 A1 Jun. 16, 2022

Related U.S. Application Data

(60) Provisional application No. 62/846,958, filed on May 13, 2019.

(51) Int. Cl.

| | |
|---|---|
| ***A61M 1/00*** | (2006.01) |
| ***A61F 13/0203*** | (2024.01) |
| ***A61F 13/05*** | (2024.01) |

(52) U.S. Cl.
CPC .......... *A61M 1/78* (2021.05); *A61F 13/0223* (2013.01); *A61F 13/05* (2024.01); *A61M 1/912* (2021.05);
(Continued)

(58) Field of Classification Search
CPC ............... A61F 13/00068; A61F 13/05; A61F 2013/00536; A61F 2013/00174; A61M 1/912; A61M 1/96
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

International Search Report and Written Opinion for Corresponding Application No. PCT/IB2020/054280 mailed Sep. 15, 2020.

(Continued)

*Primary Examiner* — Jessica Arble
*Assistant Examiner* — Meagan Ngo

(57) ABSTRACT

In some examples, a dressing suitable for treating a tissue site may include a sealing member configured to form a sealed enclosure relative to the tissue site. A fluid buffer may be configured to be positioned at a sealing member aperture in fluid communication between the sealed enclosure and an ambient environment external to the sealed enclosure. Other dressings, apparatus, systems, and methods are disclosed.

10 Claims, 10 Drawing Sheets

(52) U.S. Cl.
CPC ............ *A61M 1/915* (2021.05); *A61M 1/964* (2021.05); *A61M 1/92* (2021.05); *A61M 1/985* (2021.05); *A61M 2205/584* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Eagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0125258 | A1* | 5/2010 | Coulthard ............ A61M 1/882 604/319 |
| 2010/0185163 | A1* | 7/2010 | Heagle .................... A61F 13/05 604/290 |
| 2010/0305490 | A1* | 12/2010 | Coulthard ............ A61F 13/022 604/313 |
| 2011/0224630 | A1* | 9/2011 | Simmons ................ A61F 13/05 604/317 |
| 2011/0230849 | A1* | 9/2011 | Coulthard ............ A61M 1/962 604/319 |
| 2014/0163491 | A1 | 6/2014 | Schuessler et al. |
| 2014/0249495 | A1* | 9/2014 | Mumby ................ A61M 1/915 604/385.01 |
| 2015/0080788 | A1 | 3/2015 | Blott et al. |
| 2015/0245950 | A1* | 9/2015 | Locke .................. A61M 1/915 604/319 |
| 2016/0022885 | A1* | 1/2016 | Dunn .................... A61F 13/022 604/319 |
| 2016/0144085 | A1* | 5/2016 | Melin .................. A61M 1/915 604/319 |
| 2016/0339158 | A1* | 11/2016 | Collinson ............ A61M 1/985 |
| 2017/0189236 | A1* | 7/2017 | Locke ..................... A61M 1/80 |
| 2018/0369462 | A1* | 12/2018 | Anderson ............. A61F 13/025 |
| 2020/0107965 | A1* | 4/2020 | Greener .............. A61F 13/0243 |
| 2020/0282115 | A1* | 9/2020 | Gardner ................ A61M 1/915 |
| 2020/0337906 | A1* | 10/2020 | Long ..................... A61M 1/915 |
| 2021/0137743 | A1* | 5/2021 | Hartwell ................. A61F 13/00 |

(56) References Cited

U.S. PATENT DOCUMENTS

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| EP | 1284777 | A1 | 2/2003 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2010056977 | A2 | 5/2010 |
| WO | 2016126444 | A1 | 8/2016 |
| WO | 2019007874 | A1 | 1/2019 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its

(56) References Cited

OTHER PUBLICATIONS

Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

DRESSING INCLUDING OUTLET CONNECTION FLUID BUFFER

TECHNICAL FIELD

This disclosure relates generally to medical treatment systems and, more particularly, but not by way of limitation, to absorbent dressings, systems, and methods for treating a tissue site with reduced pressure.

BACKGROUND

Clinical studies and practice have shown that reducing pressure in proximity to a tissue site can augment and accelerate growth of new tissue at the tissue site. The applications of this phenomenon are numerous, but have proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

SUMMARY

Shortcomings with certain aspects of tissue treatment dressings, systems, and methods are addressed as shown and described in a variety of illustrative, non-limiting example embodiments herein.

In some example embodiments, a system for treating a tissue site may include a dressing, a conduit interface, a fluid buffer, and a reduced-pressure source. The dressing may include a base layer, a sealing member, and a fluid management assembly. The base layer may include a periphery surrounding a central portion and a plurality of apertures disposed through the periphery and the central portion. The sealing member may include a periphery and a central portion. The periphery of the sealing member may be positioned proximate to the periphery of the base layer. The central portion of the sealing member and the central portion of the base layer may define an enclosure. The sealing member may include a sealing member aperture in fluid communication with the enclosure. The fluid management assembly may be disposed in the enclosure and configured to absorb fluid from the tissue site. The conduit interface may be configured to be coupled to the sealing member and in fluid communication with the sealing member aperture. The fluid buffer may be configured to be positioned at the sealing member aperture in fluid communication between the conduit interface and the enclosure. The reduced-pressure source may be configured to be coupled in fluid communication with the enclosure through the conduit interface and the fluid buffer.

In some example embodiments, a dressing for treating a tissue site may include a base layer, a sealing member, and a fluid buffer. The base layer may include a periphery surrounding a central portion. The sealing member may include a periphery and a central portion, and the periphery of the sealing member may be positioned proximate to the periphery of the base layer. The central portion of the sealing member and the central portion of the base layer may define an enclosure. The sealing member may include a sealing member aperture in fluid communication with the enclosure. The fluid buffer may be configured to be positioned at the sealing member aperture in fluid communication between the enclosure and an ambient environment external to the enclosure.

In some example embodiments, a system for treating a tissue may include a dressing, a fluid buffer, and a reduced-pressure source. The dressing may include a sealing member configured to form a sealed enclosure relative to the tissue site. The sealing member may include a sealing member aperture configured to be in fluid communication with the sealed enclosure. The fluid buffer may be liquid permeable and configured to be positioned at the sealing member aperture in fluid communication between the sealed enclosure and an ambient environment external to the sealed enclosure. The reduced-pressure source may be configured to be coupled in fluid communication with the sealed enclosure through the sealing member aperture and the fluid buffer.

Other aspects, features, and advantages of the illustrative example embodiments will become apparent with reference to the drawings and detailed description that follow.

DETAILED DESCRIPTION OF EXAMPLE EMBODIMENTS

The following description of example embodiments enables a person skilled in the art to make and use the subject matter set forth in the appended claims. Certain details already known in the art may be omitted. Therefore, the following detailed description is illustrative and non-limiting.

Figure 1:
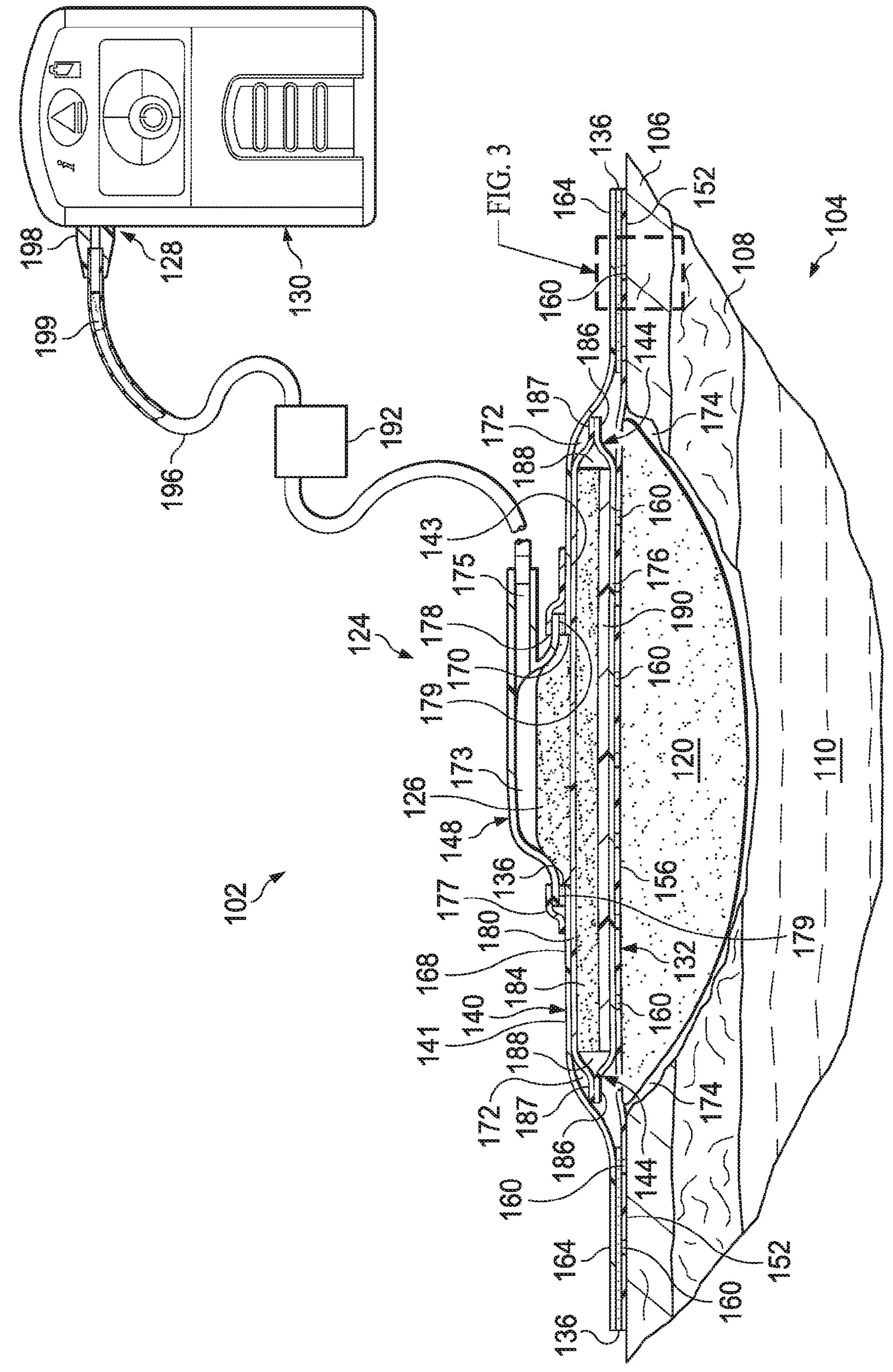
FIG. 1 is a front, cut-away view of an illustrative example embodiment of a system for treating a tissue site, depicting an example embodiment of a dressing deployed at a tissue site.

Referring to the drawings, FIG. 1 depicts an example embodiment of a system 102 for treating a tissue site 104 of a patient. The tissue site 104 may extend through or otherwise involve an epidermis 106, a dermis 108, and a subcutaneous tissue 110. The tissue site 104 may be a sub-surface tissue site as depicted in FIG. 1 that extends below the surface of the epidermis 106. Further, the tissue site 104 may be a surface tissue site (not shown) that predominantly resides on the surface of the epidermis 106, such as, for example, an incision. The system 102 may provide therapy to, for example, the epidermis 106, the dermis 108, and the subcutaneous tissue 110, regardless of the positioning of the system 102 or the type of tissue site. The system 102 may also be utilized without limitation at other tissue sites.

Further, the tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 104 may include removal of fluids, e.g., exudate or ascites.

Continuing with FIG. 1, in some embodiments, the system 102 may include an optional tissue interface, such as an interface manifold 120. Further, in some embodiments, the system 102 may include a dressing 124, a fluid buffer 126, and a reduced-pressure source 128. The reduced-pressure source 128 may be a component of an optional therapy unit 130 as shown in FIG. 1. In some embodiments, the reduced-pressure source 128 and the therapy unit 130 may be separate components. As indicated above, the interface manifold 120 is an optional component that may be omitted for different types of tissue sites or different types of therapy using reduced pressure, such as, for example, epithelialization. If equipped, the interface manifold 120 may be adapted to be positioned proximate to or adjacent to the tissue site 104, such as, for example, by cutting or otherwise shaping the interface manifold 120 in any suitable manner to fit the tissue site 104. As described below, the interface manifold 120 may be adapted to be positioned in fluid communication with the tissue site 104 to distribute reduced pressure to the tissue site 104. In some embodiments, the interface manifold 120 may be positioned in direct contact with the tissue site 104. The tissue interface or the interface manifold 120 may be formed from any manifold material or flexible bolster material that provides a vacuum space, or treatment space, such as, for example, a porous and permeable foam or foam-like material, a member formed with pathways, a graft, or a gauze. As a more specific, non-limiting example, the interface manifold 120 may be a reticulated, open-cell polyurethane or polyether foam that allows good permeability of fluids while under a reduced pressure. One such foam material is the VAC® GranuFoam® material available from Kinetic Concepts, Inc. (KCI) of San Antonio, Texas. Any material or combination of materials may be used as a manifold material for the interface manifold 120 provided that the manifold material is operable to distribute or collect fluid. For example, herein the term manifold may refer to a substance or structure that is provided to assist in delivering fluids to or removing fluids from a tissue site through a plurality of pores, pathways, or flow channels. The plurality of pores, pathways, or flow channels may be interconnected to improve distribution of fluids provided to and removed from an area around the manifold. Examples of manifolds may include, without limitation, devices that have structural elements arranged to form flow channels, cellular foam, such as open-cell foam, porous tissue collections, and liquids, gels, and foams that include or cure to include flow channels.

A material with a higher or lower density than GranuFoam® material may be desirable for the interface manifold 120 depending on the application. Among the many possible materials, the following may be used: GranuFoam® material, Foamex® technical foam, a molded bed of nails structures, a patterned grid material such as those manufactured by Sercol Industrial Fabrics, 3D textiles such as those manufactured by Baltex of Derby, U.K., a gauze, a flexible channel-containing member, a graft, etc. In some instances, ionic silver may be added to the interface manifold 120 by, for example, a micro bonding process. Other substances, such as anti-microbial agents, may be added to the interface manifold 120 as well.

In some embodiments, the interface manifold 120 may comprise a porous, hydrophobic material. The hydrophobic characteristics of the interface manifold 120 may prevent the interface manifold 120 from directly absorbing fluid, such as exudate, from the tissue site 104, but allow the fluid to pass through.

Continuing with FIG. 1, the dressing 124 may be adapted to provide reduced pressure from the reduced-pressure source 128 to the interface manifold 120, and to store fluid extracted from the tissue site 104 through the interface manifold 120. The dressing 124 may include a base layer 132, an adhesive 136, a sealing member 140, a fluid management assembly 144, and a conduit interface 148. Components of the dressing 124 may be added or removed to suit a particular application. Further, components of the dressing 124 may be included or referred to as a part of the system 102 rather than the dressing 124 itself, and components of the system 102 may be included or referred to as a part of the dressing 124. In non-limiting examples, the fluid buffer 126 and/or the conduit interface 148 may be included or referred to as a part of the system 102 or as a part of the dressing 124

Referring to FIGS. 1-5, the base layer 132 may have a periphery 152 surrounding a central portion 156, and a plurality of apertures 160 disposed through the periphery 152 and the central portion 156. The base layer 132 may also have corners 158 and edges 159. The corners 158 and the edges 159 may be part of the periphery 152. One of the edges 159 may meet another of the edges 159 to define one of the corners 158. Further, the base layer 132 may have a border 161 substantially surrounding the central portion 156 and positioned between the central portion 156 and the periphery 152. The border 161 may be free of the apertures 160.

The central portion 156 of the base layer 132 may be configured to be positioned proximate to the tissue site 104, and the periphery 152 of the base layer 132 may be configured to be positioned proximate to tissue surrounding the tissue site 104. In some embodiments, the base layer 132 may cover the interface manifold 120 and tissue surrounding the tissue site 104 such that the central portion 156 of the base layer 132 is positioned adjacent to or proximate to the interface manifold 120, and the periphery 152 of the base layer 132 is positioned adjacent to or proximate to tissue surrounding the tissue site 104. In this manner, the periphery 152 of the base layer 132 may surround the interface manifold 120. Further, the apertures 160 in the base layer 132 may be in fluid communication with the interface manifold 120 and tissue surrounding the tissue site 104.

Figure 4:
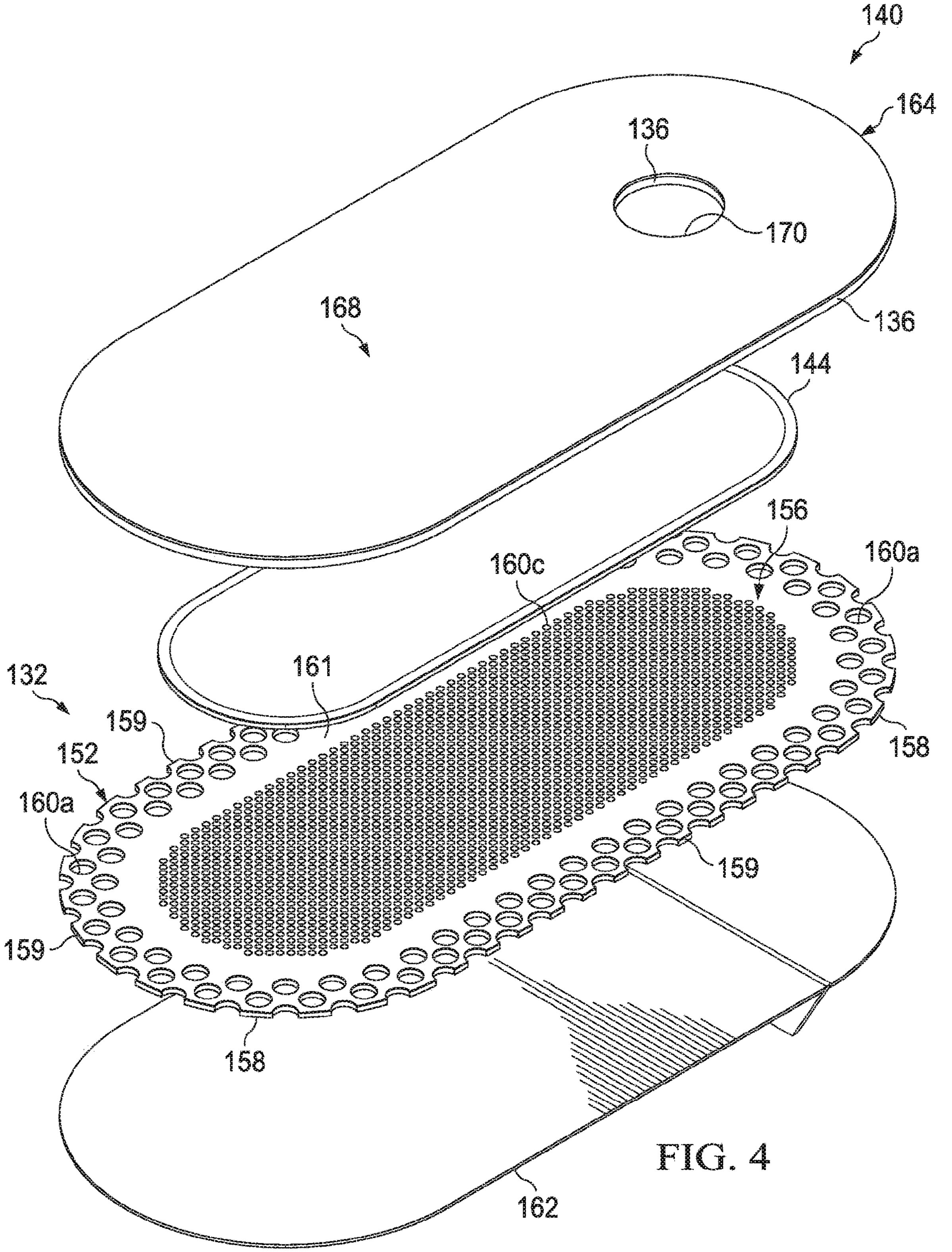
FIG. 4 is a perspective, exploded view of the example dressing of FIG. 1, depicted without a conduit interface and with an example embodiment of a release liner for protecting the dressing prior to application at a tissue site.
Figure 5:
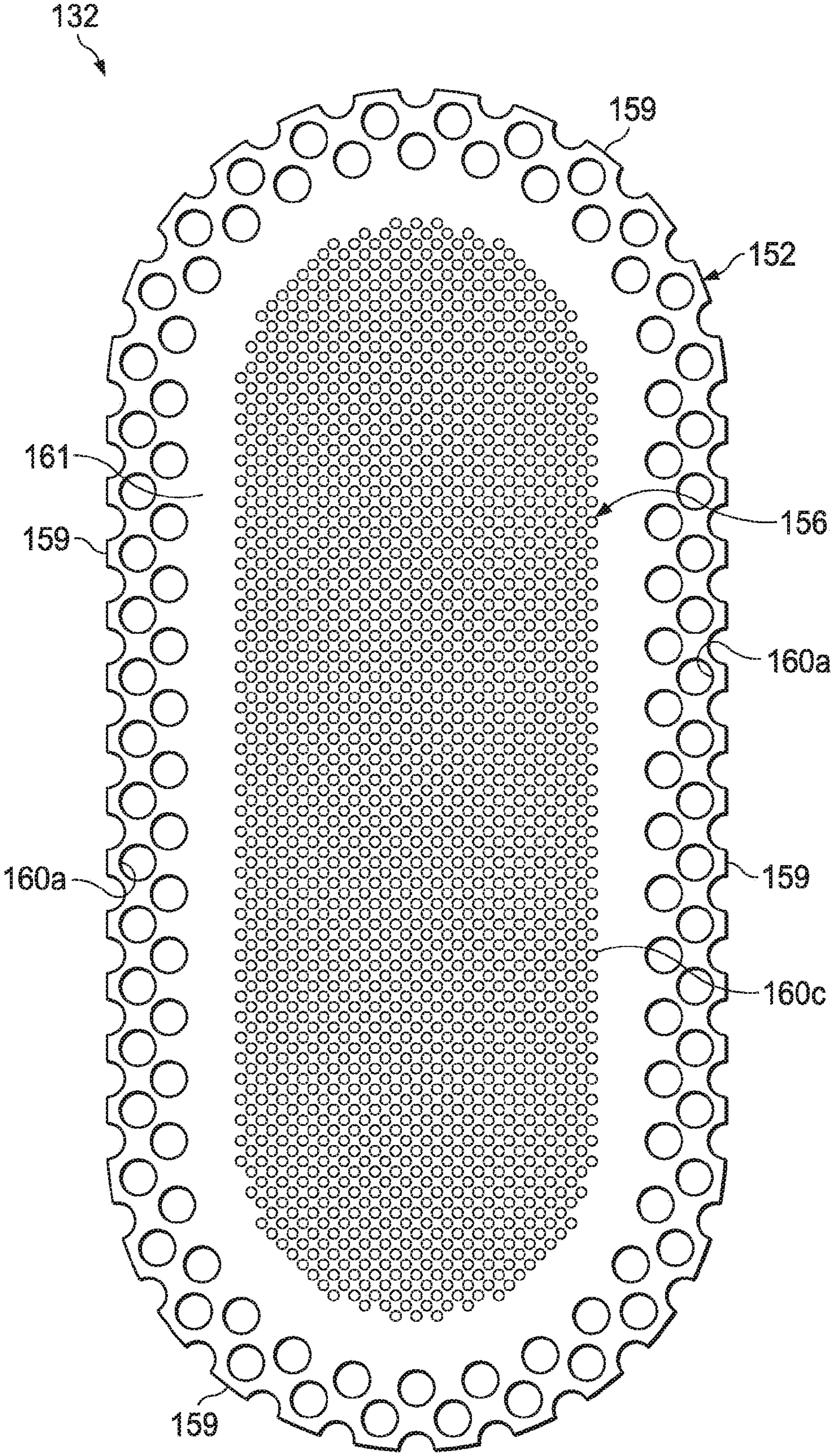
FIG. 5 is a plan view of an illustrative example embodiment of a base layer depicted with the example dressing of FIG. 4.

The apertures 160 in the base layer 132 may have any shape, such as, for example, circles, squares, stars, ovals, polygons, slits, complex curves, rectilinear shapes, triangles, or other shapes. The apertures 160 may be formed by cutting, by application of local RF energy, or other suitable techniques for forming an opening. As shown in FIGS. 4-5, each of the apertures 160 of the plurality of apertures 160 may be substantially circular in shape, having a diameter and an area. The area of each of the apertures 160 may refer to an open space or open area defining each of the apertures 160. The diameter of each of the apertures 160 may define the area of each of the apertures 160. For example, the area of one of the apertures 160 may be defined by multiplying the square of half the diameter of the aperture 160 by the value 3.14. Thus, the following equation may define the area of one of the apertures 160: Area=3.14*(diameter/2)^2. The area of the apertures 160 described in the illustrative embodiments herein may be substantially similar to the area in other embodiments (not shown) for the apertures 160 that may have non-circular shapes. The diameter of each of the apertures 160 may be substantially the same, or each of the diameters may vary depending, for example, on the position of the aperture 160 in the base layer 132. For example, the diameter of the apertures 160 in the periphery 152 of the base layer 132 may be larger than the diameter of the apertures 160 in the central portion 156 of the base layer 132. Further, the diameter of each of the apertures 160 may be about 1 millimeter to about 50 millimeters. In some embodiments, the diameter of each of the apertures 160 may be about 1 millimeter to about 20 millimeters. The apertures 160 may have a uniform pattern or may be randomly distributed on the base layer 132. The size and configuration of the apertures 160 may be designed to control the adherence of the dressing 124 to the epidermis 106 as described below.

Referring to FIGS. 4-5, in some embodiments, the apertures 160 positioned in the periphery 152 may be apertures **160*a* and the apertures 160 positioned in the central portion 156 may be apertures 160*c*. The apertures 160*a* may have a diameter between about 9.8 millimeters to about 10.2 millimeters. The apertures 160*c*** may have a diameter between about 1.8 millimeters to about 2.2 millimeters.

As shown in FIGS. 4-5, in some embodiments, the central portion 156 of the base layer 132 may be substantially oval in shape. The border 161 of the base layer 132 may substantially surround the central portion 156 and the apertures **160*c* in the central portion 156. The periphery 152 of the base layer 132 may substantially surround the border 161 and the central portion 156. Further, the periphery 152 may have a substantially oval exterior shape. Although FIGS. 4-5 depict the central portion 156, the border 161, and the periphery 152 of the base layer 132 as having a substantially oval shape, these and other components of the base layer 132** may have any shape to suit a particular application.

The base layer 132 may be a soft, pliable material suitable for providing a fluid seal with the tissue site 104 as described herein. For example, the base layer 132 may comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins coated with an adhesive described below, polyurethane, polyolefin, or hydrogenated styrenic copolymers. The base layer 132 may have a thickness between about 500 microns (μm) and about 1000 microns (μm). In some embodiments, the base layer 132 has a stiffness between about 5 Shore 00 and about 80 Shore 00. The base layer 132 may be comprised of hydrophobic or hydrophilic materials.

In some embodiments (not shown), the base layer 132 may be a hydrophobic-coated material. For example, the base layer 132 may be formed by coating a spaced material, such as, for example, woven, nonwoven, molded, or extruded mesh with a hydrophobic material. The hydrophobic material for the coating may be a soft silicone, for example. In this manner, the adhesive 136 may extend through openings in the spaced material analogous to the apertures 160 as described herein.

The adhesive 136 may be in fluid communication with the apertures 160 in at least the periphery 152 of the base layer 132. In this manner, the adhesive 136 may be in fluid communication with the tissue surrounding the tissue site 104 through the apertures 160 in the base layer 132. As described below and shown in FIG. 3, the adhesive 136 may extend through or be pressed through the plurality of apertures 160 to contact the epidermis 106 for securing the dressing 124 to, for example, the tissue surrounding the tissue site 104. The apertures 160 may provide sufficient contact of the adhesive 136 to the epidermis 106 to secure the dressing 124 about the tissue site 104. However, the configuration of the apertures 160 and the adhesive 136, described below, may permit release and repositioning of the dressing 124 about the tissue site 104.

At least one of the apertures **160*a* in the periphery 152 of the base layer 132 may be positioned at the edges 159 of the periphery 152 and may have an interior cut open or exposed at the edges 159 that is in fluid communication in a lateral direction with the edges 159. The lateral direction may refer to a direction toward the edges 159 and in the same plane as the base layer 132. As shown in FIGS. 4-5, a plurality of the apertures 160*a* in the periphery 152 may be positioned proximate to or at the edges 159 and in fluid communication in a lateral direction with the edges 159. The apertures 160*a* positioned proximate to or at the edges 159 may be spaced substantially equidistant around the periphery 152 as shown in FIGS. 4-5. However, in some embodiments, the spacing of the apertures 160*a* proximate to or at the edges 159 may be irregular. The adhesive 136 may be in fluid communication with the edges 159 through the apertures 160*a* being exposed at the edges 159. In this manner, the apertures 160*a* at the edges 159 may permit the adhesive 136 to flow around the edges 159 for enhancing the adhesion of the edges 159 around the tissue site 104**, for example.

Continuing with FIGS. 4-5, any of the apertures 160 may be adjusted in size and number to maximize the surface area of the adhesive 136 in fluid communication through the apertures 160 for a particular application or geometry of the base layer 132. For example, in some embodiments, apertures analogous to the apertures 160, having varying size, may be positioned in the periphery 152 and at the border 161. Similarly, apertures analogous to the apertures 160, having varying size, may be positioned as in other locations of the base layer 132 that may have a complex geometry or shape.

The adhesive 136 may be a medically-acceptable adhesive. The adhesive 136 may also be flowable. For example, the adhesive 136 may comprise an acrylic adhesive, rubber adhesive, high-tack silicone adhesive, polyurethane, or other adhesive substance. In some embodiments, the adhesive 136 may be a pressure-sensitive adhesive comprising an acrylic adhesive with coating weight of 15 grams/$m^2$ (gsm) to 70 grams/$m^2$ (gsm). The adhesive 136 may be a layer having substantially the same shape as the periphery 152 of the base layer 132 as shown in FIG. 4. In some embodiments, the layer of the adhesive 136 may be continuous or discontinuous. Discontinuities in the adhesive 136 may be provided by apertures (not shown) in the adhesive 136. The apertures in the adhesive 136 may be formed after application of the adhesive 136 or by coating the adhesive 136 in patterns on a carrier layer, such as, for example, a side of the sealing member 140 adapted to face the epidermis 106. Further, the apertures in the adhesive 136 may be sized to control the amount of the adhesive 136 extending through the apertures 160 in the base layer 132 to reach the epidermis 106. The apertures in the adhesive 136 may also be sized to enhance the Moisture Vapor Transfer Rate (MVTR) of the dressing 124, described further below.

Factors that may be utilized to control the adhesion strength of the dressing 124 may include the diameter and number of the apertures 160 in the base layer 132, the thickness of the base layer 132, the thickness and amount of the adhesive 136, and the tackiness of the adhesive 136. An increase in the amount of the adhesive 136 extending through the apertures 160 generally corresponds to an increase in the adhesion strength of the dressing 124. A decrease in the thickness of the base layer 132 generally corresponds to an increase in the amount of adhesive 136 extending through the apertures 160. Thus, the diameter and configuration of the apertures 160, the thickness of the base layer 132, and the amount and tackiness of the adhesive utilized may be varied to provide a desired adhesion strength for the dressing 124. For example, the thickness of the base layer 132 may be about 200 microns, the adhesive layer 136 may have a thickness of about 30 microns and a tackiness of 2000 grams per 25 centimeter wide strip, and the diameter of the apertures 160*a* in the base layer 132 may be about 10 millimeters.

In some embodiments, the tackiness of the adhesive 136 may vary in different locations of the base layer 132. For example, in locations of the base layer 132 where the apertures 160 are comparatively large, such as the apertures 160*a*, the adhesive 136 may have a lower tackiness than other locations of the base layer 132 where the apertures 160 are smaller, such as the apertures 160*c*. In this manner, locations of the base layer 132 having larger apertures 160 and lower tackiness adhesive 136 may have an adhesion strength comparable to locations having smaller apertures 160 and higher tackiness adhesive 136.

Clinical studies have shown that the configuration described herein for the base layer 132 and the adhesive 136 may reduce the occurrence of blistering, erythema, and leakage when in use. Such a configuration may provide, for example, increased patient comfort and increased durability of the dressing 124.

Referring to the embodiment of FIG. 4, a release liner 162 may be attached to or positioned adjacent to the base layer 132 to protect the adhesive 136 prior to application of the dressing 124 to the tissue site 104. Prior to application of the dressing 124 to the tissue site 104, the base layer 132 may be positioned between the sealing member 140 and the release liner 162. Removal of the release liner 162 may expose the base layer 132 and the adhesive 136 for application of the dressing 124 to the tissue site 104. The release liner 162 may also provide stiffness to assist with, for example, deployment of the dressing 124. The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the dressing 124. For example, the polar semi-crystalline polymer may be highly orientated and resistant to softening, swelling, or other deformation that may occur when brought into contact with components of the dressing 124, or when subjected to temperature or environmental variations, or sterilization. Further, a release agent may be disposed on a side of the release liner 162 that is configured to contact the base layer 132. For example, the release agent may be a silicone coating and may have a release factor suitable to facilitate removal of the release liner 162 by hand and without damaging or deforming the dressing 124. In some embodiments, the release agent may be flourosilicone. In other embodiments, the release liner 162 may be uncoated or otherwise used without a release agent.

Continuing with FIGS. 1-5, the sealing member 140 has a periphery 164 and a central portion 168. The sealing member 140 may additionally include a sealing member aperture 170, as described below. The periphery 164 of the sealing member 140 may be positioned proximate to the periphery 152 of the base layer 132 such that the central portion 168 of the sealing member 140 and the central portion 156 of the base layer 132 define an enclosure 172. The adhesive 136 may be positioned at least between the periphery 164 of the sealing member 140 and the periphery 152 of the base layer 132. The sealing member 140 may cover the tissue site 104 and the interface manifold 120 to provide a fluid seal and a sealed space 174 between the tissue site 104 and the sealing member 140 of the dressing 124. Further, the sealing member 140 may cover other tissue, such as a portion of the epidermis 106, surrounding the tissue site 104 to provide the fluid seal between the sealing member 140 and the tissue site 104. In some embodiments, a portion of the periphery 164 of the sealing member 140 may extend beyond the periphery 152 of the base layer 132 and into direct contact with tissue surrounding the tissue site 104. In other embodiments, the periphery 164 of the sealing member 140, for example, may be positioned in contact with tissue surrounding the tissue site 104 to provide the sealed space 174 without the base layer 132. Thus, the adhesive 136 may also be positioned at least between the periphery 164 of the sealing member 140 and tissue, such as the epidermis 106, surrounding the tissue site 104. The adhesive 136 may be disposed on a surface of the sealing member 140 adapted to face the tissue site 104 and the base layer 132.

The sealing member 140 may be formed from any material that allows for a fluid seal. A fluid seal is a seal adequate to maintain reduced pressure at a desired site given the particular reduced-pressure source or system involved. The sealing member 140 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 $g/m^2/24$ hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, California; polyether block polyamide copolymer (PEBAX), for example, from Arkema, France; Expopack 2327; or other appropriate material.

The sealing member 140 may be vapor permeable and/or liquid impermeable, thereby allowing vapor and inhibiting liquids from exiting the sealed space 174 provided by the dressing 124. In some embodiments, the sealing member 140 may be a flexible, breathable film, membrane, or sheet having a high MVTR of, for example, at least about 300 $g/m^2$ per 24 hours. In other embodiments, a low or no vapor transfer drape might be used. The sealing member 140 may comprise a range of medically suitable films having a thickness up to about 50 microns (μm).

Referring to FIGS. 1-2, 4, and 6A-6B, the fluid management assembly 144 may be disposed in the enclosure 172 and may include one or more wicking layers. In some embodiments, the fluid management assembly 144 may include a first wicking layer 176 and a second wicking layer 180. Further, in some embodiments, the fluid management assembly 144 may include an absorbent layer 184. The absorbent layer 184 may be positioned in fluid communication between the first wicking layer 176 and the second wicking layer 180. The first wicking layer 176 may have a grain structure adapted to wick fluid along a surface of the first wicking layer 176. Similarly, the second wicking layer 180 may have a grain structure adapted to wick fluid along a surface of the second wicking layer 180. For example, the first wicking layer 176 and the second wicking layer 180 may wick or otherwise transport fluid in a lateral direction along the surfaces of the first wicking layer 176 and the second wicking layer 180, respectively. The surfaces of the first wicking layer 176 and the second wicking layer 180 may be normal relative to the thickness of each of the first wicking layer 176 and the second wicking layer 180. The wicking of fluid along the first wicking layer 176 and the second wicking layer 180 may enhance the distribution of the fluid over a surface area of the absorbent layer 184 that may increase absorbent efficiency and resist fluid blockages. Fluid blockages may be caused by, for example, fluid pooling in a particular location in the absorbent layer 184 rather than being distributed more uniformly across the absorbent layer 184. The laminate combination of the first wicking layer 176, the second wicking layer 180, and the absorbent layer 184 may be adapted as described herein to maintain an open structure, resistant to blockage, capable of maintaining fluid communication with, for example, the tissue site 104.

In some embodiments, a peripheral portion 186 of the first wicking layer 176 may be coupled to a peripheral portion 187 of the second wicking layer 180 to define a wicking layer enclosure 188 between the first wicking layer 176 and the second wicking layer 180. In some exemplary embodiments, the wicking layer enclosure 188 may surround or otherwise encapsulate the absorbent layer 184 between the first wicking layer 176 and the second wicking layer 180.

Figure 6A:
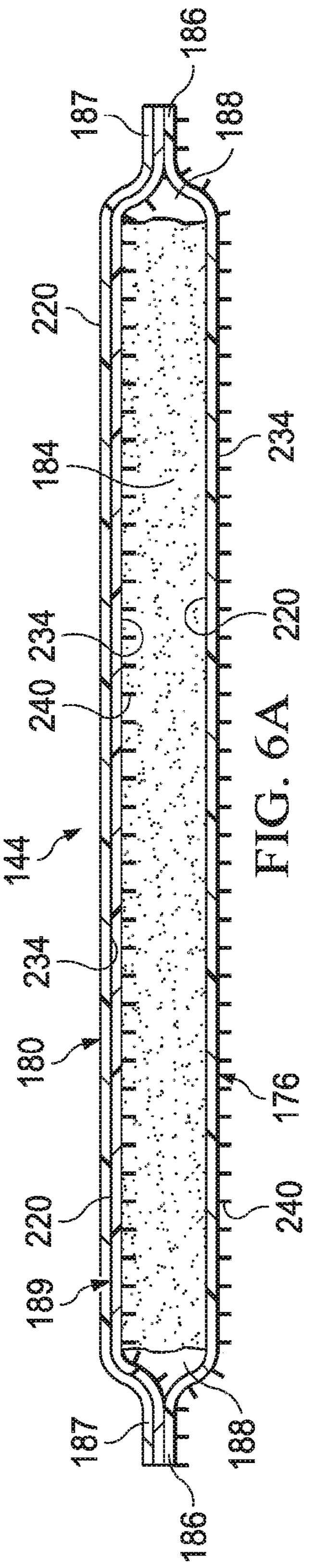
FIG. 6A is a cut-away view of an illustrative example embodiment of a fluid management assembly suitable for use with the example systems and dressings according to this disclosure.
Figure 6B:
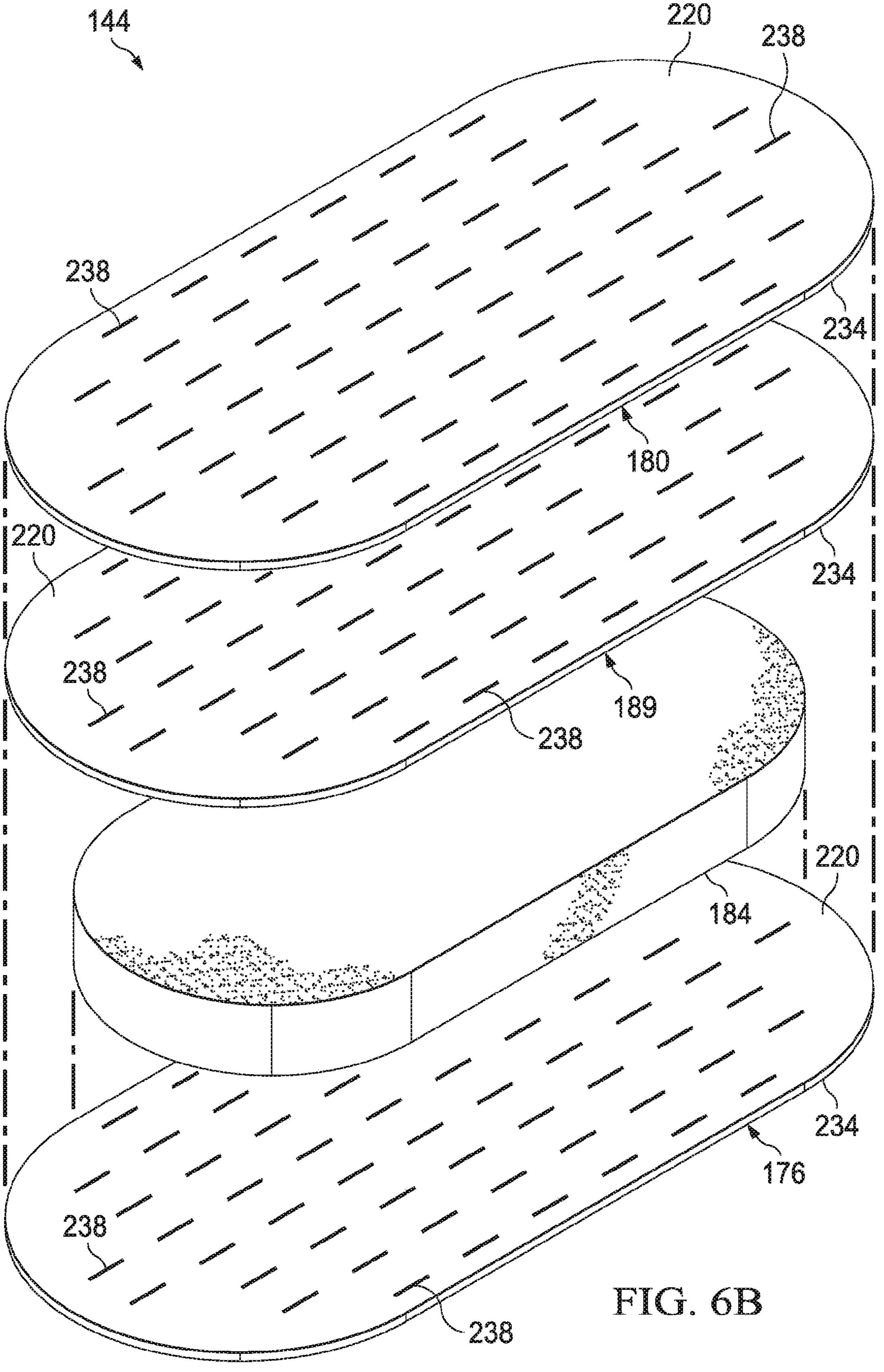
FIG. 6B is a perspective, exploded view of the example fluid management assembly of FIG. 6A.

Referring more specifically to FIGS. 6A and 6B, the fluid management assembly 144 may include, without limitation, any number of wicking layers and absorbent layers as desired for treating a particular tissue site. For example, in some embodiments, at least one intermediate wicking layer 189 may be disposed in fluid communication between the absorbent layer 184 and the second wicking layer 180. Further, including additional absorbent layers 184 may increase the absorbent mass of the fluid management assembly 144 and generally provide greater fluid capacity. However, for a given absorbent mass, multiple light coat-weight absorbent layers 184 may be utilized rather than a single heavy coat-weight absorbent layer 184 to provide a greater absorbent surface area for further enhancing the absorbent efficiency.

Each of the wicking layers 176, 180, and 189 may include a fluid distribution side 220 and a fluid acquisition side 234. The fluid distribution side 220 may be positioned facing an opposite direction from the fluid acquisition side 234. The fluid distribution side 220 may include longitudinal fibers 238 that define a grain structure. The longitudinal fibers 234 may be oriented substantially in a longitudinal direction along a length of the wicking layers 176, 180, and 189. The fluid acquisition side 234 may include vertical fibers 240, which are shown enlarged in FIG. 6A for illustrative purposes only. The vertical fibers 240 may be oriented substantially vertical or normal relative to the longitudinal fibers 238 and the length of wicking layers 176, 180, and 189. In some embodiments, the fluid acquisition side 234 of both the second wicking layer 180 and the intermediate wicking layer 189 may be positioned facing the absorbent layer 184, and the fluid acquisition side 234 of the first wicking layer 176 may be positioned facing away from the absorbent layer 184. In such an embodiment, the fluid acquisition side 234 of the second wicking layer 180 may be positioned facing the fluid distribution side 220 of the intermediate wicking layer 189, and the fluid distribution side 220 of the first wicking layer 176 may be positioned facing the absorbent layer 184.

In some embodiments, the absorbent layer 184 may be a hydrophilic material adapted to absorb fluid from, for example, the tissue site 104. Materials suitable for the absorbent layer 184 may include Luquafleece® material, Texsus FP2326, BASF 402C, Technical Absorbents 2317 available from Technical Absorbents, sodium polyacrylate super absorbers, cellulosics (carboxy methyl cellulose and salts such as sodium CMC), or alginates. Materials suitable for the first wicking layer 176 and the second wicking layer 180 may include any material having a grain structure capable of wicking fluid as described herein, such as, for example, Libeltex TDL2 80 gsm.

The fluid management assembly 144 may be a pre-laminated structure manufactured at a single location or individual layers of material stacked upon one another as described above. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161 being free of the apertures 160 as described above may provide a flexible barrier between the fluid management assembly 144 and the tissue site 104 for enhancing comfort.

Figure 2:
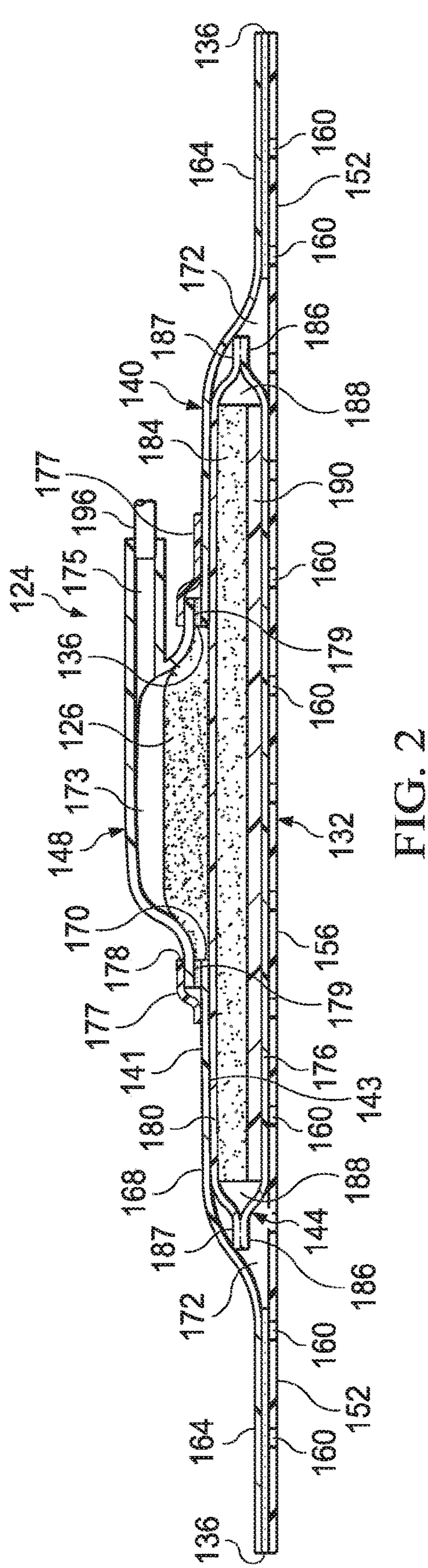
FIG. 2 is a front, cut-away view of the example dressing of FIG. 1.
Figure 3:
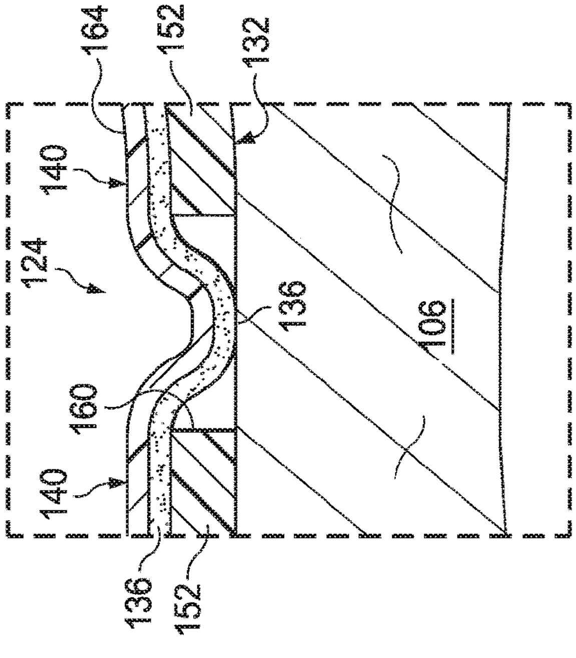
FIG. 3 is detail view taken at reference FIG. 3, depicted in FIG. 1, illustrating the example dressing of FIG. 1 positioned proximate to tissue surrounding the tissue site.
Figure 7A:
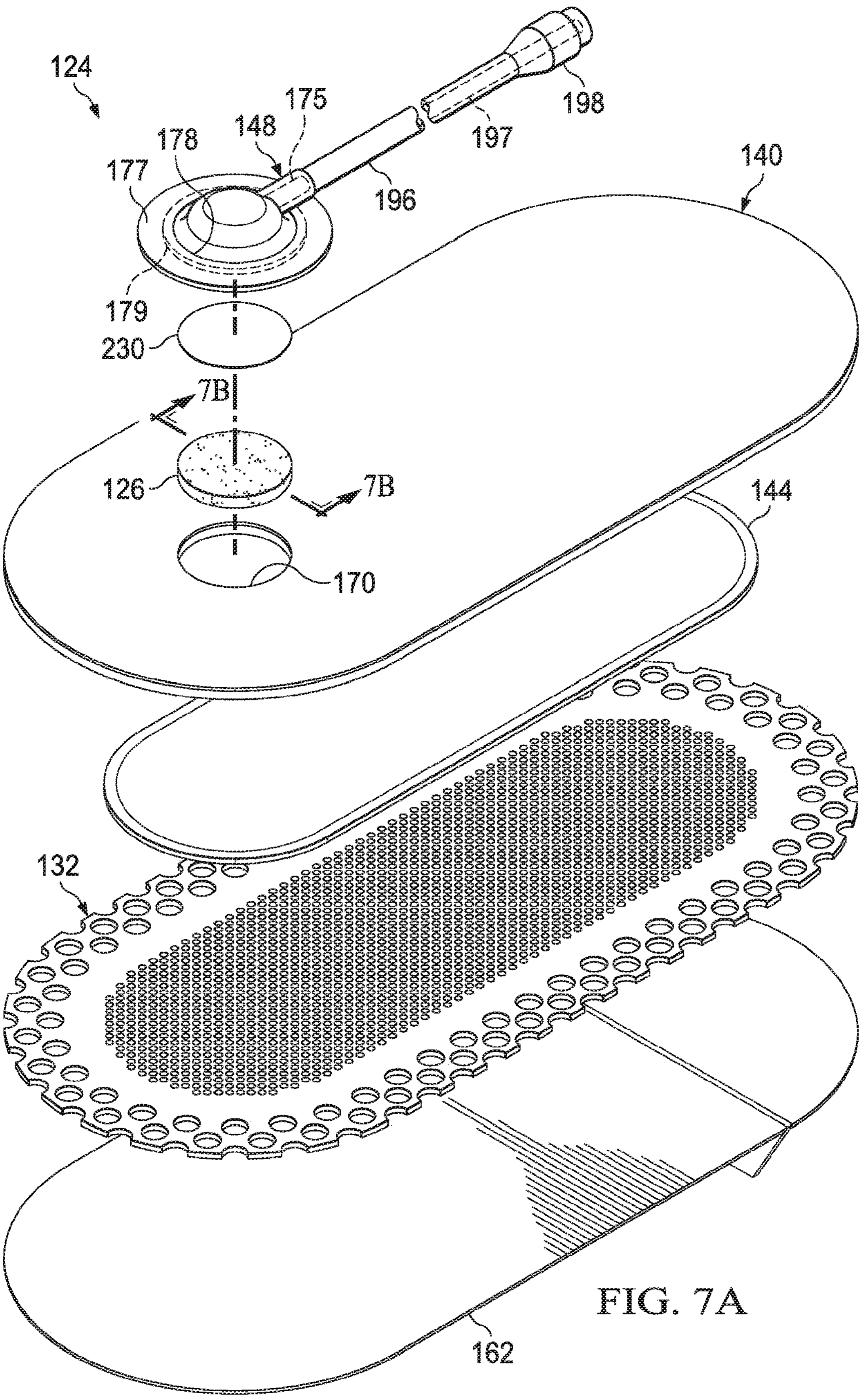
FIG. 7A is a perspective, exploded view of the example dressing of FIG. 1, depicting an illustrative example embodiment of a fluid buffer and an optional moisture indicator and shown with an example conduit interface and release liner.

Referring to FIGS. 1, 2, and 7A, the conduit interface 148 may be positioned proximate to the sealing member 140 and in fluid communication with the dressing 124 through the sealing member aperture 170 in the sealing member 140 to provide reduced pressure from the reduced-pressure source 128 to the dressing 124. Specifically, the conduit interface 148 may be positioned in fluid communication with the enclosure 172 of the dressing 124. The conduit interface 148 may also be positioned in fluid communication with the optional interface manifold 120. The conduit interface 148 may include an inlet cavity 173 in fluid communication with an outlet port 175. The inlet cavity 173 may be configured or positioned to face toward the sealing member aperture 170, and the outlet port 175 may be configured or positioned to be fluidly coupled to the reduced-pressure source 128. As shown, an optional liquid trap 192 may be positioned in fluid communication between the dressing 124 and the reduced-pressure source 128. The liquid trap 192 may be any suitable containment device having a sealed internal volume capable of retaining liquid, such as condensate or other liquids, as described below.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene, etc. In some illustrative, non-limiting embodiments, conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the dressing 124 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable for use in the system 102. Further, the absorbent material or hydrophilic polymer may be suitable for use in various components of the system 102 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 102, relative to the temperature at the tissue site 104. Removal or dissipation of liquids from the conduit interface 148 may increase visual appeal and prevent odor. Further, such removal of liquids may also increase efficiency and reliability by reducing blockages and other interference with the components of the system 102.

Similar to the conduit interface 148, the liquid trap 192, and other components of the system 102 described herein, may also be formed of an absorbent material or a hydrophilic polymer. The absorptive and evaporative properties of the hydrophilic polymer may also facilitate removal and dissipation of liquids residing in the liquid trap 192, and other components of the system 102, by evaporation. Such evaporation may leave behind a substantially solid or gel-like waste. The substantially solid or gel-like waste may be cheaper to dispose than liquids, providing a cost savings for operation of the system 102. The hydrophilic polymer may be used for other components in the system 102 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 102 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 102. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

Continuing with FIGS. 1, 2, and 7A, the reduced-pressure source 128 provides reduced pressure to the dressing 124 and the sealed space 174 and, in some embodiments, may be configured to be coupled in fluid communication with the enclosure 172 through the conduit interface 148 and the fluid buffer 126. The reduced-pressure source 128 may be any suitable device for providing reduced pressure, such as, for example, a vacuum pump, wall suction, hand pump, manual pump, electronic pump, micro-pump, piezoelectric pump, diaphragm pump, or other source. As shown in FIG. 1, the reduced-pressure source 128 may be a component of the therapy unit 130. The therapy unit 130 may include control circuitry and sensors, such as a pressure sensor, that may be configured to monitor reduced pressure at the tissue site 104. The therapy unit 130 may also be configured to control the amount of reduced pressure from the reduced-pressure source 128 being applied to the tissue site 104 according to a user input and a reduced-pressure feedback signal received from the tissue site 104.

As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site.

Unless otherwise indicated, values of pressure stated herein are gauge pressures. While the amount and nature of reduced pressure applied to a tissue site will typically vary according to the application, the reduced pressure will typically be between −5 mm Hg and −500 mm Hg, and more typically in a therapeutic range between −100 mm Hg and −200 mm Hg.

The reduced pressure delivered may be constant or varied (patterned or random), and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure corresponds to a reduction in pressure (more negative relative to ambient pressure) and a decrease in reduced pressure corresponds to an increase in pressure (less negative relative to ambient pressure).

Referring to FIGS. 1, 2, and 7A-7B, in some embodiments, the fluid buffer 126 may be configured to be positioned at the sealing member aperture 170 and in fluid communication between the conduit interface 148 and the enclosure 172. Further, in some embodiments, the fluid buffer 126 may be positioned in fluid communication between the sealed enclosure 172 and an ambient environment external to the sealed enclosure 172. Further, in some embodiments, the fluid buffer 126 may be positioned in fluid communication between an absorbent structure, such as the fluid management assembly 144, and a fluid outlet or connection point on the dressing 124, such as the sealing member aperture 170 or the conduit interface 148. In some embodiments, conduit interface 148 may be omitted, and the fluid buffer 126 may be positioned in fluid communication between the absorbent structure or the fluid management assembly 144 and a conduit or tube set fluidly coupled to the reduced-pressure source 128.

The fluid buffer 126 may be secured at the fluid outlet or connection point on the dressing 124 in various non-limiting embodiments. For example, in some embodiments, the fluid buffer 126 may be sized and configured to fit within the sealing member aperture 170 and be captured or retained between the fluid management assembly 144 and the conduit interface 148 when the conduit interface 148 is coupled to the sealing member 140 as shown in FIGS. 1, 2, and 7A. Further, in some embodiments (not shown), the fluid buffer 126 may overlap or cover the sealing member aperture 170 and be captured or retained between an exterior surface 141 of the sealing member 140 and the conduit interface 148 when the conduit interface 148 is coupled to the sealing member 140. Further, in some embodiments (not shown), the fluid buffer 126 may overlap or cover the sealing member aperture 170 and be captured or retained between an interior surface 143 of the sealing member 140 and the fluid management assembly 144 inside the sealed enclosure 172. Herein, the exterior surface 141 of the sealing member 140 is configured to face outward from the tissue site 104 and the sealed enclosure 172, and the interior surface 143 of the sealing member 140 is configured to face toward the tissue site 104 and the sealed enclosure 172. The fluid buffer 126 may extend entirely across the sealing member aperture 170 such that all fluid communication with the dressing 124 occurs through the fluid buffer 126.

The fluid buffer 126 may be both liquid permeable and gas permeable. For example, in some embodiments, the fluid buffer 126 may be permeable to gas and liquid and may be configured to have a first fluid flow resistance that is higher than a second fluid flow resistance of at least a portion of the fluid management assembly 144. Herein, a flow resistance may be referred to as a pressure drop or pressure change as fluid flows through a component. A flow resistance may be measured as a difference between an applied pressure at a first side of the component and a transmitted pressure measured at an opposing second side of the component as fluid flows through the component in an unsaturated state.

The configuration of the dressing 124 including the fluid buffer 126 may permit liquid and gas to enter, permeate, or flow into both the fluid buffer 126 and the fluid management assembly 144. However, since liquid and gas will tend to follow a path of least flow resistance, a preferential fluid flow path may be established toward the fluid management assembly 144 having the lower second fluid flow resistance compared to the higher first flow resistance of the fluid buffer 126. As result, the fluid buffer 126 may eliminate the need for a conventional liquid-air separator typically used to prevent the egress of liquid from a dressing. In contrast to a conventional liquid-air separator that is liquid impermeable, the fluid buffer 126 does not block liquid flow, but rather, creates a restriction or a delay in liquid flow or permeation, which may also encourage liquid to flow away from the fluid buffer 126 and back into the absorbent structure of the dressing 124. Accordingly, the fluid buffer 126 may be referred to as a fluid restrictor or fluid dampener that may be used instead of a conventional liquid-air separator to simplify construction, increase reliability, and reduce costs.

In some embodiments, at least a portion of the fluid buffer 126 may be configured to contact the inlet cavity 173 of the conduit interface 148 and to be positioned in fluid communication between the outlet port 175 of the conduit interface 148 and the enclosure 172 through the sealing member aperture 170. Further, in some embodiments, the fluid buffer 126 may be configured extend across one or more of the inlet cavity 173 and the outlet port 175 as a continuous layer such that substantially all fluid being communicated through the conduit interface 148 and into the sealed enclosure 172 of the dressing 124 passes through the fluid buffer 148. Further, in some embodiments, the fluid buffer 126 may be configured to be positioned between the inlet cavity 173 and the outlet port 175 of the conduit interface 148 such that fluid at the inlet cavity 173 passes through the fluid buffer 126 before exiting the outlet port 175. Further, in some embodiments, the fluid buffer 126 may be captured by one or more of the sealing member aperture 170 and the conduit interface 148.

In some embodiments, an optional adhesive, such as a pattern coat or mesh, or an adhesive analogous to the adhesive 136, may be applied to a portion of the fluid buffer 126 such as, a top or a bottom surface of the fluid buffer 126, to assist with the placement of or the securing of the fluid buffer 126 relative to other components of the system 102 or the dressing 124. Further, an optional drape ring 177 may provide additional fixation of the conduit interface 148 to the sealing member 140. For example, the drape ring 177 may include a drape ring aperture 178 sized and configured to overlap a flange 179 extending outward from and around a periphery of the conduit interface 148. A portion of the drape ring 177 may overlap and be coupled to both the sealing member 140 and a portion of an exterior surface of the flange 179 when the conduit interface 148 is coupled to the dressing 124. A portion of the conduit interface 148 may extend through the drape ring aperture 178 to provide a connection to a conduit or tube set in fluid communication with the reduced-pressure source 128. The drape ring 177 may include or be formed of similar materials described herein for the sealing member 140, such as, for example a liquid impermeable film. Further, an adhesive analogous to the adhesive 136 may be used to couple the drape ring 177 to the flange 179 of the conduit interface 148 and to the sealing member 140.

Referring to FIG. 7A, the system 102 may optionally include a moisture indicator 230 configured to indicate a change of state when in contact with moisture or a liquid. In some embodiments, the moisture indicator 230 may be positioned between the fluid buffer 126 and the outlet port 175 of the conduit interface 148 as shown in FIG. 7A. In some embodiments, the moisture indicator 230 may be positioned at, across, or covering a fluid outlet or connection point on the dressing 124, such as the sealing member aperture 170. In some embodiments (not shown), the moisture indicator 230 may be positioned between the fluid buffer 126 and a fluid outlet or connection point on the dressing 124, such as the sealing member aperture 170. In some embodiments, the moisture indicator 230 may be a membrane that changes color or becomes translucent when brought into contact with liquid. Further, in some embodiments, the moisture indicator 230 may include a dye adhered to a substrate, such as a layer of filter paper or a wicking material. In some embodiments, the moisture indicator 230 may include or be formed of an ink or wax coating on a surface of the fluid buffer 126.

Figure 7B:
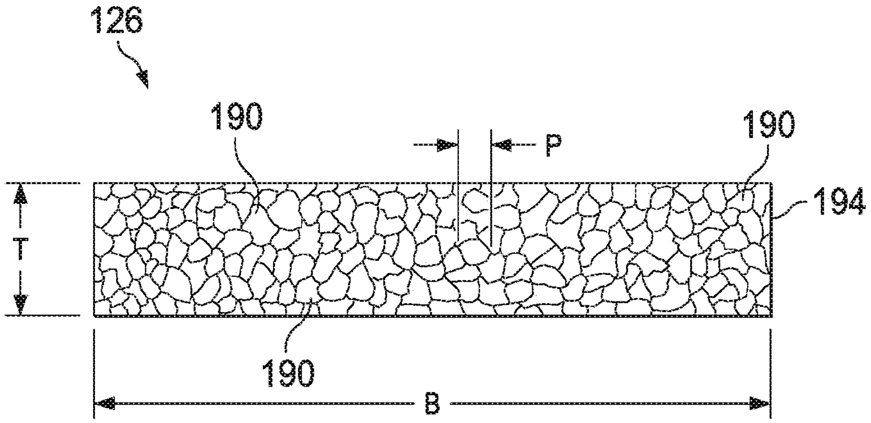
FIG. 7B is a detail view of the example fluid buffer, taken at reference line 7B-7B shown in FIG. 7A.

Referring to FIG. 7B, in some embodiments, the fluid buffer 126 may include or be a porous material or a foam material, which may be, for example, a porous hydrophobic foam. The porous material of the fluid buffer 126 may include pores 190 and may have the first flow resistance by itself as a material property, for example, or in cooperation with other elements of the fluid buffer 126 described herein. By way of example and without limitation, the porous material or foam material for the fluid buffer 126 may include or be formed of the following materials: a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; polyvinyl butyral (PVB); or a bioabsorbable polymer, examples of which include polylactic acid, polylactide (PLA), polyglycolic acid, polyglycolide (PGA), and polycaprolactone (PCL).

In some embodiments, the fluid buffer 126 may have a diameter B between about 25 millimeters to about 40 millimeters. Further, in some embodiments, the fluid buffer 126 may include an average pore diameter P between about 0.05 millimeters to about 0.3 millimeters. Further, in some embodiments, the fluid buffer 126 may include a porosity between about 120 pores per inch (ppi) to about 350 pores per inch (ppi). Other materials may form the fluid buffer 126 or part of the fluid buffer 126.

In some embodiments, the fluid buffer 126 may include or be a porous material that has been treated or modified to provide the first flow resistance that is higher than the second flow resistance of the fluid management assembly 144. For example, the fluid buffer 126 may include a porous foam that is felted in a felting process to form a felted foam layer 194. In some embodiments, the felted foam layer 194 may be felted to a ratio between about 1:3 to about 1:7. Further, in some embodiments, the felted foam layer 194 may be felted to a thickness T between about 2 millimeters to about 6 millimeters. Further, in some embodiments, the felted foam layer 194 may include the average pore diameter P between about 0.05 millimeters to about 0.3 millimeters. Further, in some embodiments, the felted foam layer 194 may include a porosity between about 120 pores per inch (ppi) to about 350 pores per inch (ppi).

The felted foam layer 194 may be formed by any known methods of felting, which may include applying heat and pressure to a porous material or foam material. Such methods may include compressing the porous material between one or more heated platens for a specified period of time and at a specified temperature. The porosity of the felted foam layer 194 between about 120 pores per inch (ppi) to about 350 pores per inch (ppi) may be measured in or along the direction of compression between the two platens or along the thickness T of the felted foam layer 194 shown in FIG. 7B, for example.

In some embodiments, the period of time of compression may range between 15 and 30 minutes, though the time period may be more or less depending on the specific type of porous material used. In some embodiments, the temperature may range between 160° C. and 180° C. Generally, the lower the temperature of the platen, the longer porous material must be held in compression. After the specified time period has elapsed, the pressure and heat will form a felted structure or surface on or through the porous material. The felted structure may be comparatively smoother than any unfinished or non-felted surface or portion of the porous material. Further, the pores in the felted structure may be smaller than the pores throughout any unfinished or non-felted surface or portion of the porous material. In some embodiments, the felted structure may be applied to all surfaces or portions of the porous material. Further, in some embodiments, the felted structure may extend into or through an entire thickness of the porous material such that the all of the porous material is felted.

Felting may be expressed as a ratio of the uncompressed thickness of the porous material to the compressed or final thickness of the porous material after the felting process has taken place. For example, a felting ratio of 1:3 compresses the porous material to one-third of an uncompressed thickness of the porous material. A felting ratio of 1:7 compresses the porous material to one-seventh of an uncompressed thickness of the porous material. In some embodiments, the compressed thickness of the porous material may be less than one-tenth, one-ninth, one-eighth, one-seventh, one-sixth, one-fifth, one-fourth, or one-third of the uncompressed thickness of the porous material.

Figure 8:
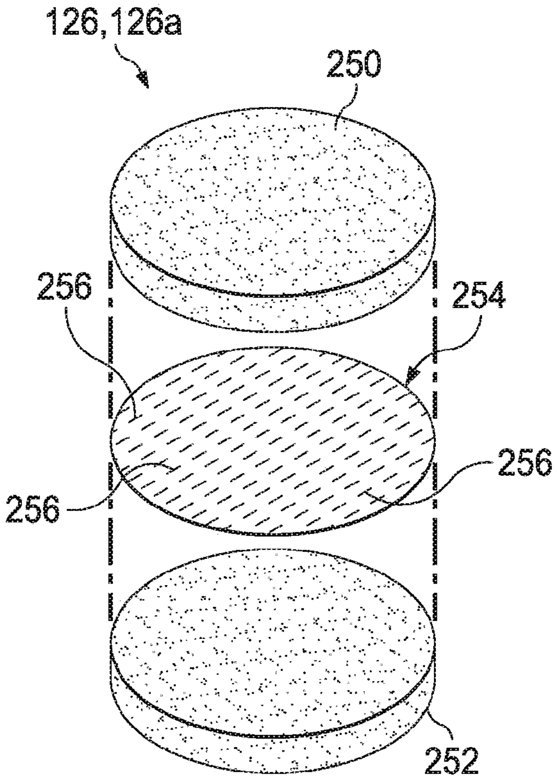
FIG. 8 is a perspective, exploded view of another illustrative example embodiment of a fluid buffer.

Referring to FIG. 8, in some embodiments, the fluid buffer 126 may be a fluid buffer **126*a*. The fluid buffer 126*a* may include a first foam layer 250, a second foam layer 252, and a fenestrated film layer 254 positioned between the first foam layer 250 and the second foam layer 252. The fenestrated film layer 254 may include or be formed of analogous materials set forth herein for the sealing member 140, such as a liquid impermeable film. The fenestrated film layer 254 may include fenestrations 256 disposed through the liquid impermeable film forming at least a portion of the fenestrated film layer 254. The liquid impermeable film may block the passage of liquid and the fenestrations 256 may permit the passage of liquid through the fenestrated film layer 254. In some embodiments, one or both of the first foam layer 250 and the second foam layer 252 may be felted. In such an embodiment, the first foam layer 250 and/or the second foam layer 252 may be a felted foam layer analogous to the felted foam layer 194**.

Figure 9:
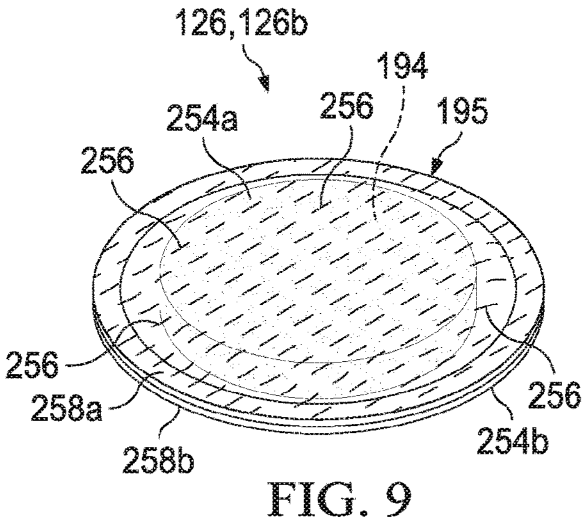
FIG. 9 is a perspective view of yet another illustrative example embodiment of a fluid buffer.

Referring to FIG. 9, in some embodiments, the fluid buffer 126 may be a fluid buffer 126*b* and may include the felted foam layer 194 encapsulated by a fenestrated film 195. In some embodiments, the fenestrated film 195 may include or be a first fenestrated film layer 254*a* and a second fenestrated film layer 254*b*, and the felted foam layer 194 may be positioned between the first fenestrated film layer 254*a* and the second fenestrated film layer 254*b*. The first fenestrated film layer 254*a* and the second fenestrated film layer 254*b* may include the fenestrations 256 and be formed of analogous materials as the fenestrated film layer 254. A first periphery 258*a* of the first fenestrated film layer 254*a* may be coupled to a second periphery 258*b* of the second fenestrated film layer 254*b* around the felted foam layer 194 to encapsulate or surround the felted foam layer 194. In some embodiments (not shown), the fluid buffer 126*b* may include an un-felted foam layer analogous to the first felted foam layer 250 encapsulated by the fenestrated film 195 or the first film layer 254*a* and the second film layer 254*b*. In such an embodiment, the felted foam layer 194 shown in FIG. 9 may be removed and replaced with an un-felted foam layer analogous to the first foam layer 250.

Figure 10:
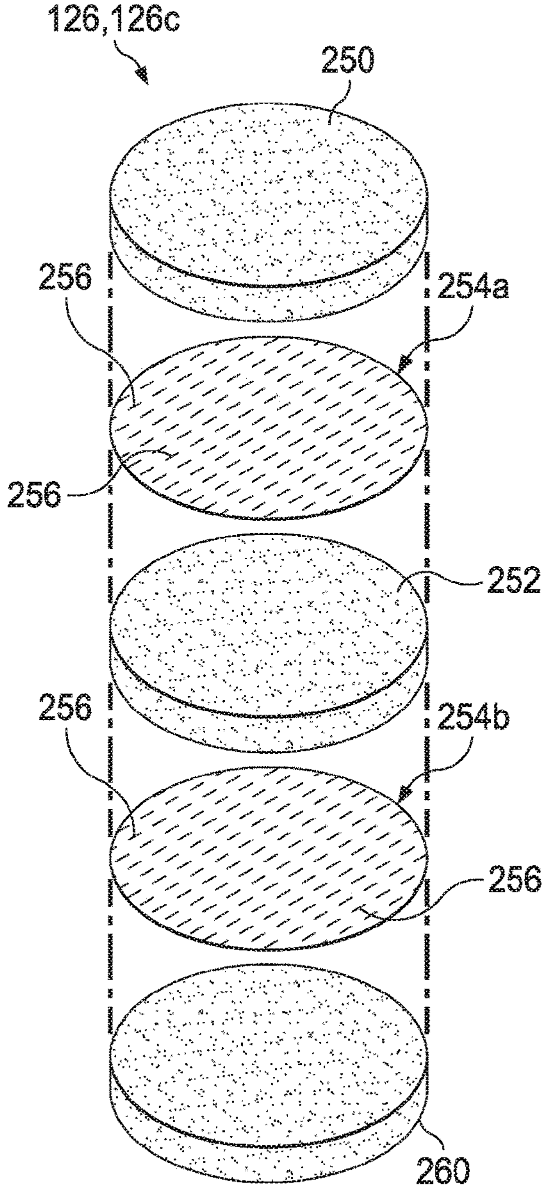
FIG. 10 is a perspective, exploded view of yet another illustrative example embodiment of a fluid buffer.

Referring to FIG. 10, in some embodiments, the fluid buffer 126 may be a fluid buffer 126*c*. The fluid buffer 126*c* may include the first fenestrated film layer 254*a* and the second fenestrated film layer 254*b*, which may include the fenestrations 256 and may be formed of analogous materials as the fenestrated film layer 254. Further, the system 102 or the fluid buffer 126*c* may additionally include a third foam layer 260. In the fluid buffer 126*c* embodiment, the first fenestrated film layer 254*a* may be positioned between the first foam layer 250 and the second foam layer 252. Further, the second fenestrated film layer 254*b* may be positioned between the second foam layer 252 and the third foam layer 260. In some embodiments, one or more of the first foam layer 250, the second foam layer 252, and the third foam layer 260 may be felted. In such an embodiment, the first foam layer 250 and/or the second foam layer 252 and/or the third foam layer 260 may be a felted foam layer analogous to the felted foam layer 194.

Testing has shown that dressings including the fluid buffer 126 outperformed conventional dressings that use a conventional liquid-air separator to prevent liquid from exiting the dressing and entering a tube set or conduit that is typically used to communicate reduced pressure to the dressing from a reduced pressure source. The conventional dressings in the testing included a liquid-air separator formed from a membrane or layer having a water break pressure greater than the operating pressure of the reduced pressure source used to supply reduced pressure to the dressings. For example, the liquid-air separator in the conventional dressings had a water break pressure of about 200 mm Hg or greater and an average pore size of 1 micron or 0.001 millimeters. The liquid-air separator in the conventional dressings was positioned at an outlet of the dressing configured to be fluidly coupled to a tube set or conduit for communicating reduced pressure. In contrast to the liquid-air separator in the conventional dressings, the dressing 124 does not use a liquid-air separator positioned at the dressing 124. Instead, the dressing 124 includes the fluid buffer 126, which does not have a significant water break pressure and includes the average pore diameter P between about 0.05 millimeters to about 0.3 millimeters or about 50 microns to about 300 microns.

During the testing, two conventional dressings were tested against two dressings analogous to the dressing 124 including the fluid buffer 126 according to this specification. All of the tested dressings had a 60 ml liquid capacity. Liquid was delivered to each dressing at a high rate in stages while each dressing was monitored for pressure drop and liquid egress from the dressing into a tube set between the dressing and a reduced pressure source. Signs of pressure drop and/or liquid egress from a dressing was considered a dressing failure.

Initially, 10 ml of liquid was delivered to each dressing in 2 minutes followed by a 2 minute hold. This process was repeated after the initial 2 minute hold by delivering another 10 ml of liquid to each dressings in 2 minutes followed by another 2 minute hold. Both of the conventional dressings experienced a failure by allowing liquid to exit the dressing and to enter the tube set while also experiencing a pressure drop. The dressings 124 including the fluid buffer 126 did not experience a pressure drop or liquid entering the tube set.

After the initial 20 ml of liquid delivery, liquid delivery re-commenced at a rate of 1 ml/min for 8 minutes in which another 8 ml of liquid was delivered to each dressing. The conventional dressings again experienced a failure with liquid exiting the dressing after the 8 ml of liquid was delivered. The dressings 124 had not allowed liquid to egress, had not experienced a pressure drop, and had not otherwise failed. At this point in the testing, the conventional dressings and the dressings 124 had each received 28 ml of liquid delivered in 12 minutes.

After a 10 minute hold, liquid delivery re-commenced at a rate of 0.5 ml/min. After 3 ml of liquid was delivered to each dressing, the conventional dressings again failed. Liquid delivery to each of the dressings continued. After 10 ml of liquid was delivered, one of the dressings 124 experienced a pressure drop and fluid could be seen migrating through the fluid buffer 126. The other test dressing 124 had still not failed. At this stage, each of the dressings had received 40 ml of liquid.

In summary, testing has shown that the use of the fluid buffer 126 extended the point of failure of the dressings 124 by 100% compared to the conventional dressings. Further, when one of the dressings 124 experienced a pressure drop and fluid migrating into the fluid buffer 126, this dressing 124 recovered when the delivery of liquid stopped, after which the liquid was wicked back into the absorbent structure of the dressing, permitting pressure to be re-established.

Referring now to FIGS. 1 and 7A, a conduit 196 having an internal lumen 197 may be coupled in fluid communication between the reduced-pressure source 128 and the dressing 124. The internal lumen 197 may have an internal diameter between about 0.5 millimeters to about 3.0 millimeters. More specifically, the internal diameter of the internal lumen 197 may be about 1 millimeter to about 2 millimeters. The conduit interface 148 may be coupled in fluid communication with the dressing 124 and adapted to connect between the conduit 196 and the dressing 124 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The sealing member aperture 170 in the sealing member 140 may provide fluid communication between the dressing 124 and the conduit interface 148. Specifically, the conduit interface 148 may be in fluid communication with the enclosure 172 or the sealed space 174 through the sealing member aperture 170 in the sealing member 140 and through the fluid buffer 126. In some embodiments, the conduit 196 may be inserted into the dressing 124 through the sealing member aperture 170 in the sealing member 140 to provide fluid communication with the reduced-pressure source 128 without use of the conduit interface 148. The reduced-pressure source 128 may also be directly coupled in fluid communication with the dressing 124 or the sealing member 140 without use of the conduit 196. The conduit 196 may be, for example, a flexible polymer tube. A distal end of the conduit 196 may include a coupling 198 for attachment to the reduced-pressure source 128.

The conduit 196 may have an optional hydrophobic filter 199 disposed in the internal lumen 197 such that fluid communication between the reduced-pressure source 128 and the dressing 124 is provided through the hydrophobic filter 199. The hydrophobic filter 199 may be comprised of a material that is liquid impermeable and vapor permeable. In some embodiments, the hydrophobic filter 199 may comprise a material manufactured under the designation MMT-314 by W.L. Gore & Associates, Inc. of Newark, Delaware, United States, or similar materials. In some embodiments, the hydrophobic filter 199 may be provided in the form of a membrane or layer. In some embodiments, the hydrophobic filter 199 may be, for example, a porous, sintered polymer cylinder sized to fit the dimensions of the internal lumen 197 to substantially preclude liquid from bypassing the cylinder. The hydrophobic filter 199 may also be treated with an absorbent material adapted to swell when brought into contact with liquid to block the flow of the liquid. The hydrophobic filter 199 may be positioned at any location within the internal lumen 197. However, positioning the hydrophobic filter 199 within the internal lumen 197 closer toward the reduced-pressure source 128, rather than the dressing 124, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application. More specifically, a length of about 1 foot or 304.8 millimeters may provide enough absorbent and evaporative surface area to suit many applications, and may provide a cost savings compared to longer lengths. If an application requires additional length for the conduit 196, the absorbent hydrophilic polymer may be coupled in fluid communication with a length of conduit formed of a non-absorbent hydrophobic polymer to provide additional cost savings.

In operation of the system 102 according to some illustrative embodiments, the optional interface manifold 120 may be disposed against or proximate to the tissue site 104. The dressing 124 may then be applied over the interface manifold 120 and the tissue site 104 to form the sealed space 174. Specifically, the base layer 132 may be applied covering the interface manifold 120 and the tissue surrounding the tissue site 104. In embodiments that omit the interface manifold 120, the dressing 124 may be applied over, in contact with, or covering the tissue site 104 and tissue around the tissue site 104.

The materials described above for the base layer 132 have a tackiness that may hold the dressing 124 initially in position. The tackiness may be such that if an adjustment is desired, the dressing 124 may be removed and reapplied. Once the dressing 124 is in the desired position, a force may be applied, such as by hand pressing, on a side of the sealing member 140 opposite the tissue site 104. The force applied to the sealing member 140 may cause at least some portion of the adhesive 136 to penetrate or extend through the plurality of apertures 160 and into contact with tissue surrounding the tissue site 104, such as the epidermis 106, to releaseably adhere the dressing 124 about the tissue site 104. In this manner, the configuration of the dressing 124 described above may provide an effective and reliable seal against challenging anatomical surfaces, such as an elbow or heal, at and around the tissue site 104. Further, the dressing 124 permits re-application or re-positioning to, for example, correct air leaks caused by creases and other discontinuities in the dressing 124 and the tissue site 104. The ability to rectify leaks may increase the reliability of the therapy and reduce power consumption.

As the dressing 124 comes into contact with fluid from the tissue site 104, the fluid moves through the apertures 160 toward the fluid management assembly 144. The fluid management assembly 144 wicks or otherwise moves the fluid through the interface manifold 120 and away from the tissue site 104. As described above, the interface manifold 120 may be adapted to communicate fluid from the tissue site 104 rather than store the fluid. Thus, the fluid management assembly 144 may be more absorbent than the interface manifold 120. The fluid management assembly 144 being more absorbent than the interface manifold 120 provides an absorbent gradient through the dressing 124 that attracts fluid from the tissue site 104 or the interface manifold 120 to the fluid management assembly 144. Thus, in some embodiments, the fluid management assembly 144 may be adapted to wick, pull, draw, or otherwise attract fluid from the tissue site 104 through the interface manifold 120. In the fluid management assembly 144, the fluid initially comes into contact with the first wicking layer 176. The first wicking layer 176 may distribute the fluid laterally along the surface of the first wicking layer 176 as described above for absorption and storage within the absorbent layer 184. Similarly, fluid coming into contact with the second wicking layer 180 may be distributed laterally along the surface of the second wicking layer 180 for absorption within the absorbent layer 184.

Figure 11A:
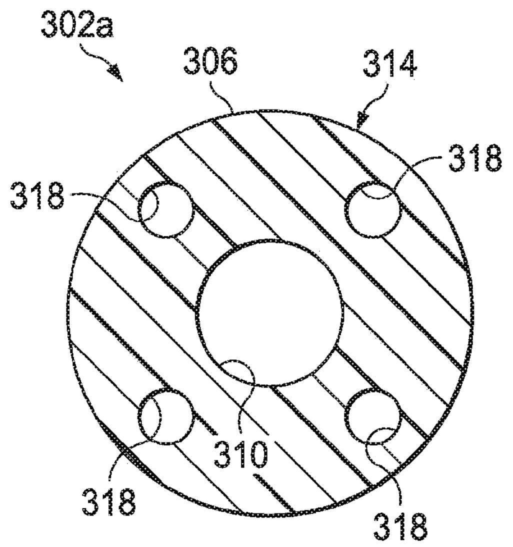
FIG. 11A is a cross-sectional view of an illustrative example embodiment of a multi-lumen conduit suitable for use with the example systems and dressings according to this disclosure.
Figure 11B:
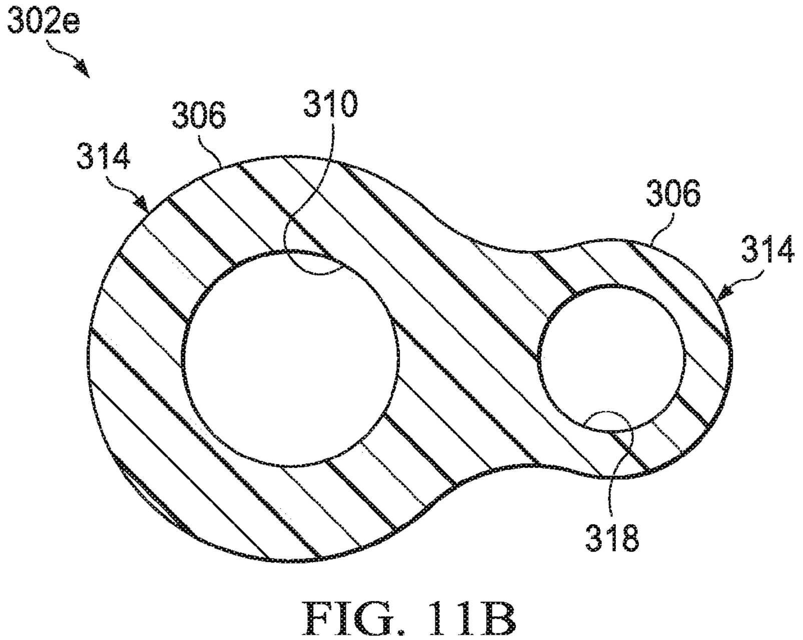
FIG. 11B is a cross-sectional view of another illustrative example embodiment of a multi-lumen conduit suitable for use with the example systems and dressings according to this disclosure.

Referring to FIGS. 11A-11B, in some embodiments, the conduit 196 may be a multi-lumen conduit 302. For example, FIG. 11A depicts an illustrative embodiment of a multi-lumen conduit **302*a*. The multi-lumen conduit 302*a* may have an external surface 306, a primary lumen 310, a wall 314, and at least one secondary lumen 318. The wall 314 may carry the primary lumen 310 and the at least one secondary lumen 318. The primary lumen 310 may be substantially isolated from fluid communication with the at least one secondary lumen 318 along the length of the multi-lumen conduit 302*a*. Although shown in FIG. 11A as having a substantially circular cross-section, the external surface 306 of the multi-lumen conduit 302*a* may have any shape to suit a particular application. The wall 314 of the multi-lumen conduit 302*a* may have a thickness between the primary lumen 310 and the external surface 306. As depicted in FIG. 11A, the at least one secondary lumen 318 may be four secondary lumens 318 carried by the wall 314 substantially parallel to the primary lumen 310 and about a perimeter of the primary lumen 310. The secondary lumens 318 may be separate from one another and substantially isolated from fluid communication with one another along the length of the multi-lumen conduit 302***a*. Further, the secondary lumens 318 may be separate from the primary lumen 310 and substantially isolated from fluid communication with the primary lumen 310. The secondary lumens 318 may also be positioned concentric relative to the primary lumen 310 and substantially equidistant about the perimeter of the primary lumen 310. Although FIG. 11A depicts four secondary lumens 318, any number of secondary lumens 318 may be provided and positioned in any suitable manner for a particular application.

Similar to the internal lumen 197 of the conduit 196, the primary lumen 310 may be coupled in fluid communication between the reduced-pressure source 128 and the dressing 124 as described above. In some embodiments, the primary lumen 310 may be coupled in fluid communication between the conduit interface 148 and the reduced-pressure source 128. Further, analogous to the internal lumen 197, reduced pressure may be provided through the primary lumen 310 from the reduced-pressure source 128 to the dressing 124. In some embodiments, the primary lumen 310 may be configured to extract fluid such as exudate from the tissue site 104. The secondary lumens 318 may be coupled in fluid communication between the therapy unit 130 and the dressing 124. In some embodiments, the at least one secondary lumen 318 may be coupled in fluid communication between the conduit interface 148 and the therapy unit 130. Further, the secondary lumens 318 may be in fluid communication with the primary lumen 310 at the dressing 124 and configured to provide a reduced-pressure feedback signal from the dressing 124 to the therapy unit 130. For example, the secondary lumens 318 may be in fluid communication with the primary lumen 310 at the conduit interface 148 or other component of the dressing 124.

The multi-lumen conduit 302*a* may be comprised of an absorbent material or hydrophilic polymer, such as, for example, the absorbent material or the hydrophilic polymer described above in connection with the conduit interface 148, the conduit 196, and the coupling 198. The absorbent material or the hydrophilic polymer may be vapor permeable and liquid impermeable. In some embodiments, at least a portion of the wall 314 and the external surface 306 of the multi-lumen conduit 302*a* may be comprised of the absorbent material or the hydrophilic polymer. In this manner, the multi-lumen conduit 302*a* may permit liquids, such as condensate, in the multi-lumen conduit 302*a* to evaporate, or otherwise dissipate, as described above. For example, the absorbent material or the hydrophilic polymer may allow the liquid to pass through the multi-lumen conduit 302*a* as vapor, in a gaseous phase, and evaporate into the atmosphere external to the multi-lumen conduit 302*a*. Liquids such as exudate from the tissue site 104 may also be evaporated or dissipated through the multi-lumen conduit 302*a* in the same manner. This feature may be advantageous when the optional therapy unit 130 is used for monitoring and controlling reduced pressure at the tissue site 104. For example, liquid present in the secondary lumens 318 may interfere with a reduced-pressure feedback signal being transmitted to the therapy unit 130 through the secondary lumens 318. The use of the hydrophilic polymer for the multi-lumen conduit 302*a* may permit removal of such liquid for enhancing the visual appeal, reliability, and efficiency of the system 102. After evaporation of liquid in the multi-lumen conduit 302*a*, other blockages from, for example, desiccated exudate, solids, or gel-like substances that were carried by the evaporated liquid may be visible for further remediation. Further, the use of the hydrophilic polymer as described herein may reduce the occurrence of skin damage caused by moisture buildup between components of the system 102, such as the multi-lumen conduit 302*a*, and the skin of a patient.

Referring to FIG. 11B, depicted is an illustrative embodiment of a multi-lumen conduit 302*e* having an oblong cross section. Similar to the multi-lumen conduit 302*a*, the multi-lumen conduit 302*e* may have the external surface 306, the primary lumen 310, the wall 314, and the at least one secondary lumen 318. However, FIG. 11B depicts the at least one secondary lumen 318 of the multi-lumen conduit 302*e* as a single secondary lumen 318 that may be carried by the wall 314 beside the primary lumen 310. Such a configuration may provide a substantially flat, low profile shape that may enhance user comfort and may increase the flexibility of the multi-lumen conduit 302*e*. For example, in this configuration, the multi-lumen conduit 302*e* may be routed through tight spaces with reduced risk of kinking or blockages of fluid communication. Although not depicted, additional lumens may be added in this substantially flat configuration, laterally disposed from the primary lumen 310 and the secondary lumen 318, as necessary to suit a particular application. The above features described in connection with the multi-lumen conduits 302*a* and 302*e* may be used in combination with one another to suit a particular application.

The appended claims set forth novel and inventive aspects of the subject matter in this disclosure. While shown in several illustrative embodiments, a person having ordinary skill in the art will recognize that the systems, apparatuses, and methods described herein are susceptible to various changes and modifications. Features may be emphasized in some example embodiments while being omitted in others, but a person of skill in the art will appreciate that features described in the context of one example embodiment may be readily applicable to other example embodiments. Further, certain features, elements, or aspects may be omitted from this disclosure if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims. Moreover, descriptions of various alternatives using terms such as "or" do not require mutual exclusivity unless clearly required by the context, and the indefinite articles "a" or "an" do not limit the subject to a single instance unless clearly required by the context.

We claim:

1. A system for treating a tissue site, comprising:

a dressing, comprising:

a base layer including a periphery surrounding a central portion and a plurality of apertures disposed through the periphery and the central portion, a sealing member including a periphery and a central portion, the periphery of the sealing member positioned proximate to the periphery of the base layer, the central portion of the sealing member and the central portion of the base layer defining an enclosure, the sealing member including a sealing member aperture in fluid communication with the enclosure, and a fluid management assembly disposed in the enclosure and configured to absorb fluid from the tissue site;

a conduit interface configured to be coupled in contact with the sealing member and including an inlet cavity and an outlet port in fluid communication with the sealing member aperture;

a fluid buffer comprising a foam configured to be positioned in direct contact with the sealing member aperture, at least a portion of the foam positioned continuously across the conduit interface relative to at least one of the inlet cavity or the outlet port such that all fluid communication between the outlet port of the conduit interface and the enclosure passes through the portion of the foam of the fluid buffer, wherein the fluid buffer is permeable to gas and liquid and is configured to have a first fluid flow resistance that is higher than a second fluid flow resistance of at least a portion of the fluid management assembly; and a reduced-pressure source configured to be coupled in fluid communication with the enclosure through the conduit interface and the fluid buffer.

2. The system of claim 1, wherein the fluid buffer comprises a felted foam layer.

3. The system of claim 2, wherein the felted foam layer comprises a porosity between about 120 pores per inch to about 350 pores per inch.

4. The system of claim 2, wherein the felted foam layer is encapsulated by a fenestrated film.

5. The system of claim 1, wherein the fluid buffer comprises a first foam layer, a second foam layer, and a fenestrated film layer positioned between the first foam layer and the second foam layer.

6. The system of claim 5, wherein the fenestrated film layer comprises a liquid impermeable film including fenestrations disposed through the liquid impermeable film, and wherein the liquid impermeable film blocks the passage of liquid and the fenestrations permit the passage of liquid through the fenestrated film layer.

7. The system of claim 5, wherein the fenestrated film layer is a first fenestrated film layer, wherein the system further comprises a second fenestrated film layer and a third foam layer, and wherein the second fenestrated film layer is positioned between the second foam layer and the third foam layer.

8. The system of claim 1, wherein the inlet cavity is configured face the sealing member aperture and the outlet port is configured to be fluidly coupled to the reduced-pressure source.

9. The system of claim 8, further comprising a moisture indicator configured to indicate a change of state when in contact with a liquid, wherein the moisture indicator is positioned between the fluid buffer and the outlet port of the conduit interface.

10. The system of claim 1, further comprising an adhesive configured to extend through the apertures at least in the periphery of the base layer to contact tissue surrounding the tissue site, wherein the adhesive is disposed on a surface of at least the periphery of the sealing member that is configured to face the base layer.

* * * * *